United States Patent [19] [11] Patent Number: 4,835,319
Corbin et al. [45] Date of Patent: May 30, 1989

[54] PROCESS FOR THE MANUFACTURE OF 1,4-BIS(4-PHENOXYBENZOYL)BENZENE WITH A ZEOLITE CATALYST

[75] Inventors: David R. Corbin, West Chester, Pa.; Enio Kumpinsky; Antonio Vidal, both of Wilmington, Del.

[73] Assignee: E. I. Du Pont de Nemours and Company, Wilmington, Del.

[21] Appl. No.: 218,941

[22] Filed: Jul. 14, 1988

Related U.S. Application Data

[63] Continuation-in-part of Ser. No. 117,991, Nov. 9, 1987, abandoned.

[51] Int. Cl.$^4$ .............................................. C07C 45/46
[52] U.S. Cl. ................................................... 568/322
[58] Field of Search ........................ 568/319, 322, 323

[56] References Cited

U.S. PATENT DOCUMENTS

| | | | |
|---|---|---|---|
| 3,169,942 | 2/1965 | Pike | 260/465 |
| 3,254,131 | 5/1966 | Landis | 260/613 |
| 3,454,596 | 7/1969 | Hamilton | 260/327 |
| 3,496,239 | 2/1970 | Hamilton et al. | 260/619 |
| 4,294,987 | 10/1981 | Prather et al. | 564/331 |
| 4,304,941 | 12/1981 | Lee et al. | 568/319 |
| 4,423,259 | 12/1983 | Kobayashi et al. | 570/144 |
| 4,474,988 | 10/1984 | Kaiser | 564/508 |
| 4,474,990 | 10/1984 | Jansons | 568/322 |
| 4,511,681 | 4/1985 | Yoshida et al. | 523/310 |
| 4,647,418 | 10/1986 | Ford et al. | 564/479 |
| 4,668,826 | 5/1987 | Gupta | 568/319 |

Primary Examiner—James H. Reamer
Attorney, Agent, or Firm—Paul R. Steyermark

[57] ABSTRACT 1,4-Bis(4-phenoxybenzoyl)benzene is made in a heterogeneous system by a reaction of diphenyl ether with 1,4-benzenedicarbonyl chloride at 190°–250° C. in the presence of a zeolite catalyst having a ring structure containing 12 oxygen atoms, which can be either an activated zeolite in hydrogen form or an iron-exchanged zeolite, which zeolite can be readily separated from the hot liquid phase in the reaction mixture. The mole ratio of diphenyl ether to 1,4-dicarbonyl chloride, when the catalyst is in hydrogen form, is about 50–80:1; when the catalyst is in iron-exchanged form, it is about 10–50:1, and the weight ratio of 1,4-benzenedicarbonyl chloride to zeolite in hydrogen form is 3:1 to 1:2, while the ratio of 1,4-benzenedicarbonyl chloride to zeolite in iron-exchanged form is 10:1 to 1:32. The product readily crystallizes in a high state of purity from the cooled solution. 1,4-Bis(4-phenoxybenzoyl)benzene is a vaulable intermediate in the synthesis of polyetherketone resins.

16 Claims, No Drawings

PROCESS FOR THE MANUFACTURE OF 1,4-BIS(4-PHENOXYBENZOYL)BENZENE WITH A ZEOLITE CATALYST

CROSS-REFERENCE TO RELATED APPLICATION

This is a continuation-in-part of our copending application Ser. No. 07/117,991, filed Nov. 9, 1987 now abandoned.

BACKGROUND OF THE INVENTION

This invention relates to a process for the manufacture of 1,4-bis(4-phenoxybenzoyl)benzene (sometimes referred to hereinafter as BPBB) in a hetereogeneous system, in the presence of a zeolite catalyst, which can be readily separated from the liquid phase in the reaction mixture.

BPBB, which is an important intermediate in the preparation of polyetherketone resins, can be made by condensation of 1,4-benzenedicarbonyl chloride with diphenyl ether in the presence of a Friedel-Crafts catalyst, usually aluminum chloride, which is employed in an amount of at least three moles per mole of 1,4-benzenedicarbonyl chloride. Diphenyl ether normally is used in a significant excess to minimize formation of higher oligomers. Normally, the reaction is carried out in a solvent such as, e.g., 1,2-dichlorobenzene, at a temperature of approximately $-10°$ C. After the reaction is complete, methanol is added to precipitate the product and remove aluminum chloride therefrom. The product is filtered off, washed repeatedly with methanol, and recrystallized from N,N-dimethylacetamide.

Use of aluminum chloride catalyst presents various shortcomings. Aluminum chloride, which is soluble in hot 1,2-dichlorobenzene, tends to contaminate the BPBB product, thus requiring repeated washings for its removal from the product and finally recrystallization of BPBB. The recovered aluminum chloride cannot be reused and this creates a waste disposal problem as well as adds to the cost of the operation. Finally, aluminum chloride does not have a high para-isomer selectivity, so that it tends to also produce a fair proportion of the ortho-isomer, i.e., [1-(2-phenoxy),4-(4-phenoxy)]dibenzoylbenzene, which by ring closure leads to the formation of 9-phenylxanthydrol, as discussed in U.S. Pat. No. 3,767,620 to Angelo.

It would be desirable to be able to produce BPBB in a simpler operation, which would result in a good yield of a high purity material free of ortho-isomer and catalyst contamination, so that the additional purification steps could be avoided, and the overall reaction yield could be increased.

SUMMARY OF THE INVENTION

According to this invention, there is now provided a process for the manufacture of BPBB, said process comprising contacting diphenyl ether for a period of about 40-360 min at a temperature of about 190°-250° C. with 1,4-benzenedicarbonyl chloride in the presence of a zeolite selected from the group consisting of:

(a) activated zeolites in hydrogen-exchanged form having a ring structure containing 12 oxygen atoms and belonging to one of the classes of naturally occurring faujasites, naturally occurring mordenites, synthetic zeolites Y, and synthetic mordenites, and (b) iron-exchanged zeolites having a ring structure containing 12 oxygen atoms and belonging to one of the classes of naturally occurring faujasites, naturally occurring mordenites, synthetic zeolites X and Y, and synthetic mordenites, the weight ratio of 1,4-benzenedicarbonyl chloride to hydrogen-exchanged zeolite being about 3:1 to 1:2, and to iron-exchanged zeolite about 10:1 to 1:2, and the mole ratio of diphenyl ether to 1,4-benzenedicarbonyl chloride being about 15-80:1, when a hydrogen-exchanged zeolite is the catalyst and about 10-50:1 when an iron-exchanged zeolite is the catalyst, separating the zeolite from the resulting hot solution, cooling the hot solution to a temperature at which BPBB crystallizes, and separating the crystalline product from the cooled solution.

DETAILED DESCRIPTION OF THE INVENTION

The basic reaction involved in the process of this invention is shown in the following equation:

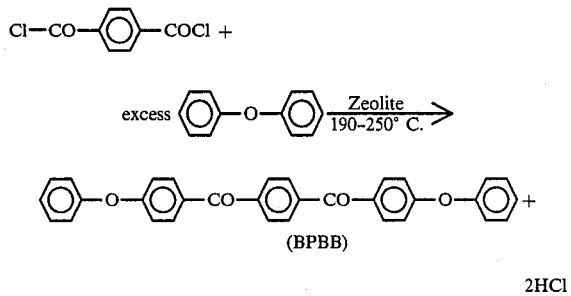

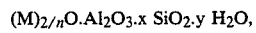

2HCl

The starting materials for this reaction are well known and readily available.

1,4-Benzenedicarbonyl chloride, also known as terephthalyl chloride, can be made from terephthalic acid by any suitable known reaction, e.g., with phosphorus pentachloride, phosphorus trichloride, or thionyl chloride. 1,4-Benzenedicarbonyl chloride also is commercially available, i.a., from E. I. du Pont de Nemours and Company.

Diphenyl ether is commercially available, i.a., from Dow Chemical Company.

Suitable zeolites, as has been stated above, must satisfy certain requirements. Generally speaking, zeolites are complex aluminosilicates characterized by a three-dimensional framework structure enclosing cavities occupied by ions and water molecules, all of which can move with significant freedom within the zeolite matrix. In commercially useful zeolites, water molecules can be removed from or replaced within the framework without destroying its geometry. Most zeolites useful in the process of the present invention can be represented by the following formula:

$(M)_{2/n}O \cdot Al_2O_3 \cdot x\ SiO_2 \cdot y\ H_2O$, wherein M is a cation of valence n; x is 2 or greater; and y is an empirical number determined by the porosity and hydration of the zeolite, generally from 2 to 8. In naturally occurring zeolites, M is principally represented by Na, Ca, K, Mg, and Ba in proportions approximately corresponding to their geochemical abundance. The cation M is loosely bound to the structure and frequently can be completely or partially replaced with hydrogen or with another cation by conventional ion exchange. When M is completely or predominantly hydrogen, the zeolite is said to be in hydrogen form.

The zeolite structure consists of corner-linked tetrahedra containing Al or Si atoms in the center and O atoms at the corners. Those tetrahedra are combined in well-defined repeating structures comprising various combinations of 4-, 5-, 6-, 8-, 10-, and 12-membered oxygen-containing rings. It is generally understood by chemists familiar with zeolites that a term such as "12-membered ring" means a ring containing twelve atoms of oxygen, and such terminology will be sometimes used in this description.

The resulting framework consists of regular channels and cages which impart a useful pore structure for catalysis. Pore dimensions are determined by the geometry of the aluminosilicate tetrahedra forming the zeolite channels or cages, with nominal openings from about 2.6 A for six-membered rings to about 7.4 A for twelve-membered rings. For the purpose of this invention, the ring must be twelve-membered. In faujasite and in synthetic zeolites X and Y, the nominal pore size will be about 7.4 A; in the mordenites, it is about 6.7–7 A. The actual pore size, however, may vary to some extent, depending on such factors as the degree of hydration or the presence and location of metal ions. The actual pore size may be determined, if desired, as described in R. M. Barrer, *Hydrothermal Chemistry of Zeolites*, Chapter 1, pp. 20–27, Academic Press, New York, 1982. All the suitable zeolites will be able to absorb within their pore structure the BPBB molecule, which has an estimated size of 25 A length, 8 A width, and 6.5 A thickness.

Further information on zeolites may be obtained from: Meier et al. *Atlas of Zeolite Structure Types*, International Zeolite Association, Pittsburgh, 1978; and Smith, "Origin and Structure of Zeolites" in *Zeolite Chemistry and Catalysis*, pp. 1–79, ACS Monograph 171, American Chemical Society, Washington, D.C., 1976. Also see U.S. Pat. Nos. 3,904,738 (H. E. Robson) and 4,613,720 (C. Bonifaz et al.).

The zeolites used in the process of this invention may be either in the hydrogen-exchanged form or in the iron-exchanged form, except that zeolite X can be used only in the iron-exchanged form. The hydrogen-exchanged form, or hydrogen form, may be obtained, among others, by ammonium exchange followed by calcination, by direct ion exchange with a mineral acid, or by hydrolysis of polyvalent cations. It is believed that acid sites present in these zeolites are responsible for their catalytic activity. For a discussion of acid sites in zeolites, see Dwyer, "Zeolite Structure, Composition, and Catalysis", *Chemistry and Industry*, Apr. 2, 1984, pp. 258–269.

Generally speaking, these acid sites can be either of the Bronstedt (proton-donating) type or of the Lewis (electron pair accepting) type, and either type may predominate. However, for the purpose of this invention, it does not appear important which type of acid sites predominates. It has been found that zeolites exchanged with polyvalent metals other than iron, such as, e.g., cobalt, nickel, zinc, or rhodium, are ineffective as catalysts in the BPBB synthesis. It further has been found that, although iron-exchanged zeolite X is a very good catalyst, the hydrogen-exchanged zeolite X is not useful at all. The main difference between zeolite X and zeolite Y lies in their respective silicon oxide/aluminum oxide mole ratios. For zeolite X, this ratio is about 2.5, while for zeolite Y, it is about 5. Mordenites have a ratio greater than 10. It is believed that hydrogen exchange of zeolite X, followed by activation, destroys the crystal structure of this material and converts it largely to a noncrystalline aluminosilicate, which is incapable of catalyzing the BPBB synthesis.

Suitable zeolites in hydrogen form include certain commercial materials known under the designations SK-500, ELZ-20, and M-8 mordenite, sold by Union Carbide Corporation and "Zeolon" 900H mordenite sold by PQ Corporation. These zeolites can be in powder or pellet form. Preferred zeolites in hydrogen form are ELZ-20 and mordenites, both of which can be regenerated. While ELZ-20 and SK-500 have cage structures, mordenites have channel-shaped pores. The typical chemical composition of the above four zeolites is given below:

| Chemical Component | Anhydrous SK-500 | Weight ELZ-20 | Percent M-8 | "Zeolon" 900H |
|---|---|---|---|---|
| $Na_2O$ | 1.6 | 0.2 | 0.1 | — |
| $SiO_2$ | 65.0 | 76.9 | 90.6 | 90.9 |
| $Al_2O_3$ | 22.7 | 20.9 | 8.5 | 9.1 |
| $RE_2O_3$* | 10.7 | — | — | — |
| $SiO_2/Al_2O_3$ mole ratio | 4.9 | 6.2 | 18.1 | 17.0 |

*Rare earth oxide

Commercial zeolites, in their hydrogen form, are normally activated by the manufacturer, e.g., when they are converted from ammonium to hydrogen form by heating in air. Exposing an activated zeolite to ambient moisture reduces its activity, which can be restored by heating to drive out the adsorbed water.

In the practical operation of the process of this invention, the reactants and the zeolite catalyst are charged into the reactor, and the temperature is raised to the desired range either at atmospheric pressure or at a reduced pressure. While a large excess of diphenyl ether is necessary, it is preferred to keep the diphenyl ether/1,4-benzenedicarbonyl chloride mole ratio, when a zeolite in the hydrogen form is used, within the range of 40–50:1. The preferred reaction temperature is 220°–250° C. Within this temperature range, the preferred reaction time is about 60–150 min. The most preferred reaction conditions are 120 min at 250° C. Generally, if the process temperature is too low, conversion of the starting materials to the desired product, BPBB, will be reduced below a commercially attractive level. If the temperature is too high, conversion may also be reduced because of some catalyst deactivation.

Following the removal of some zeolite catalysts in hydrogen form, the catalysts can be regenerated and reused. Regeneration is accomplished by calcining the catalyst in the presence of air at a temperature of about 500°–700° C. for several hours, preferably for about 7 hours. When such a catalyst can be regenerated and reused, an additional benefit is realized. So far, it has not been possible, however, to regenerate the SK-500 zeolite.

Iron-exchanged zeolite catalysts are preferred because they can be reused repeatedly without regeneration. Their activity and selectivity are improved by heating several hours with hydrogen chloride to a high temperature, e.g., 250° C. Iron-exchanged zeolites are described, i.a., by C. Naccache et al., in *Zeolites: Science and Technology*, Ribeiro et al. Eds., Martinus Nijhoff, The Hague, 1984, pp. 373–396; and by B. Wichterlova et al. in *Metal Microstructures in Zeolites*, Jacobs et al.

Eds., Elsevier, Amsterdam, 1982, pp. 143–150. When an iron-exchanged zeolite is used as the catalyst, the preferred weight ratio of 1,4-benzenedicarbonyl chloride to zeolite is about 6:1, while the preferred mole ratio of diphenyl ether to 1,4-benzenedicarbonyl chloride is about 15–20:1.

BPBB, which crystallizes from the solution in diphenyl ether after cooling, is of sufficiently high purity to be used without recrystallization for the final step of making a polyetherketone by condensation with additional dicarboxylic acid chloride in a manner known to the art. The preferred temperature to which the solution is cooled and at which BPBB is isolated is about 25°–40° C.

Excess diphenyl ether can be reused several times without purification. When purification is deemed advisable, this is done most conveniently by distillation at a reduced pressure.

While the above description concerns a batch process of this invention, the process can be adapted to a continuous operation, where the critical variables to be controlled are the weight ratio of 1,4-benzenedicarbonyl chloride to zeolite, the mole ratio of diphenyl ether to 1,4-benzenedicarbonyl chloride, temperature, and residence time. Various routine operations can be modified in both the batch process and the continuous process so as to obtain the greatest operational efficiency; e.g., separation of solids from liquids can be achieved not only by filtration but also by decantation or centrifugation, whichever is the most convenient, i.a., from the standpoint of time, energy requirement, and equipment available.

This invention is now illustrated by representative examples of certain preferred embodiments thereof. In all the examples, the conversion of 1,4-benzenedicarbonyl chloride to BPBB was calculated as follows:

$$\text{conversion (\%)} = \frac{\text{moles of BPBB in the product}}{\text{moles of 1,4-benzenedicarbonyl chloride in the feed}} \times 100$$

Any partial reaction product, comprising one molecule of each reactant, that may have been formed as a side product was disregarded.

The purity of BPBB product was determined either by differential scanning calorimetry (DSC) or by nuclear magnetic resonance (NMR), or by both DSC and NMR.

EXAMPLE 1

A 12-member ring zeolite, H-Y ELZ-20 (from Union Carbide Co.) was calcined in air by heating to 500° C. at a rate of 60° C./hr and holding at 500° C. for 10 hr. It was then allowed to cool to 100° C. and was stored in a sealed glass jar.

A mixture of 134 g (0.787 mole) of diphenyl ether and 2 g of the above zeolite was heated to 250° C. in a reactor with a nitrogen purge. The zeolite color changed from white to red. 1,4-Benzenedicarbonyl chloride, 3 g (0.0148 mole), was added to the reactor and 6 hr later the zeolite was filtered from the hot solution. The filtrate was allowed to cool, and crystals of BPBB began precipitating at about 115° C. The product was filtered at 30° C., washed with methanol, and dried. It weighed 4.34 g, for a conversion of 62.1%. The purity of the BPBB product was greater than 99% (by DSC and NMR).

COMPARATIVE EXAMPLE 1 AND EXAMPLE 2

The procedure of Example 1 was repeated with the same amounts of the same materials except that two different reaction temperatures were used, namely, 180° C. and 200° C. At 180° C., conversion in Comparative Example 1 was only 19.5%; and in Example 2, at 200° C., it was 31.3%. The conditions of Comparative Example 1 are outside the scope of this invention. The conversion obtained in Example 2 is marginally acceptable.

COMPARATIVE EXAMPLE 2

An 8-membered ring zeolite H-Rho was prepared as follows. A mixture of 200 ml of a 4M solution of Na$_2$AlO$_2$OH, 50 ml of a 50 wt. % solution of CsOH and 26 g of NaOH was added to 720 ml of colloidal silica ("Ludox" LS 30, Du Pont) in a polytetrafluoroethylene bottle and allowed to stand at 25° C. for nine days. The mixture was heated to 100° C. and kept at that temperature for 7 days, allowed to stand at 25° C. for three more days, and reheated at 100° C. for 24 hours. This product was washed and then soaked overnight three times in a 20 wt. % solution of ammonium nitrate to produce an ammonium-Rho zeolite. This was converted to the hydrogen form by heating in air to 550° C. at a rate of 60° C./hr and holding at that temperature for 7 hours. It was then cooled to 100° C. and sealed from the atmosphere.

A mixture of 134 g (0.787 mole) of diphenyl ether and 2 g of the above zeolite was heated to 250° C. and held at 250° C. for 30 min under nitrogen purge. The color of the zeolite remained white. 1,4-Benzenedicarbonyl chloride (3 g, 0.0148 mole) was added, and heating was continued for 6 hr. The color of the zeolite remained white during that time. The zeolite was filtered from the hot solution, but no crystalline material precipitated in the filtrate. It was determined by distillation of diphenyl ether that conversion to BPBB was less than 1%. This example shows that an 8-membered ring zeolite structure is not a satisfactory catalyst in this process.

COMPARATIVE EXAMPLE 3

A sample of a 10-membered sodium, TPA-ZSM-5 zeolite was prepared by the method of Rollman et al. (*Inorg. Synth.*, 1983, vol. 22, pp. 61–69) and heated in a flow of air at 60° C./hr to 550° C., then held at 550° C. for 10 hours. This zeolite was exchanged three times with a 10 wt. % ammonium nitrate solution at 90° C. for one hour, heated at 500° C. for 7 hours, and then cooled to 100° C. and sealed from the atmosphere.

A mixture of 134 g (0.787 mole) of diphenyl ether, 2 g of the above H-ZSM-5 zeolite, and 3 g (0.0148 mole) of 1,4-benzenedicarbonyl chloride was heated to 250° C. with a nitrogen purge. The zeolite color changed from white to red. The temperature was kept at 250° C. for two hours, and the zeolite was filtered off from the hot solution. The solid product, which precipitated on cooling of the filtrate, was separated by filtration at 30° C. A conversion of 5.8% was obtained, but the BPBB product contained many unidentified impurities. This example shows that a 10-membered zeolite is not a satisfactory catalyst in this process.

COMPARATIVE EXAMPLE 4

A total of 5.61 g of commercial acidic alumina catalyst (ICN Biochemicals, catalog No. 02099) was added to 67.4 g (0.4 mole) of diphenyl ether and 4.15 g (0.02 mole) of 1,4-benzenedicarbonyl chloride in a reactor, and the mixture was heated under nitrogen for one hour at 250° C. The acidic alumina was filtered off; the filtrate was cooled to 30° C. and refiltered. Only 1.34 g of dry, impure product was obtained. This example shows that acidic alumina is not a satisfactory catalyst for this process.

EXAMPLE 3

The procedure of Example 1 was repeated with the same amounts of the starting materials, except that the catalyst was an SK-500 zeolite (from Union Carbide Co.), which first had been calcined in air at 50° C. for 7 hr, cooled to 100° C., and sealed from the atmosphere. The conversion to BPBB was 62%. The BPBB product was determined to be more than 99% pure (by DSC).

COMPARATIVE EXAMPLE 5

The procedure of Example 1 was repeated with the same amounts of the starting materials, except that 1,3-benzenedicarbonyl chloride was used instead of 1,4-benzendicarbonyl chloride. No condensation product was isolated. This example shows that the zeolite-catalyzed reaction is selective with respect to position isomers.

EXAMPLES 4, 5, AND 6

Zeolites M-8, ELZ-20, and SK-500 were activated by heating in air at 800° C. for 10 hr, cooled to 100° C., and sealed from the atmosphere. Each of those catalysts was used in an experiment according to Example 1 with the same amounts of the starting materials, except that the reaction time in each case was 2 hr. The respective conversions were as follows:

| | |
|---|---|
| M-8 | 32% |
| ELZ-20 | 67% |
| SK-500 | 66%. |

EXAMPLE 7

Zeolite ELZ-20 was heated in air at 700° C. for 7 hr, then cooled to 100° C. and sealed. This catalyst was used in the process of Example 1, except that the reaction was carried out at a pressure of about 21 kPa, at which diphenyl ether was refluxing at 195° C. BPBB was obtained at a conversion of 56%.

EXAMPLE 8

A mixture of 240 g of SK-500 zeolite activated by the manufacturer, 15 L (16 kg, 94 moles) of diphenyl ether, and 360 g (1.77 moles) of 1,4-benzenedicarbonyl chloride was heated to 250° C. and held at that temperature for 8 hr. The temperature was lowered to 150° C., and the liquid was decanted from the zeolite. The decanted liquid was cooled to 30° C. The precipitated BPBB was filtered off, but it contained red solid impurities caused by inefficient decantation from zeolite. It was washed with methanol and stored. This experiment was repeated three more times under the same conditions, and the products of all four runs were combined. The combined product was recrystallized from 1,2-dichlorobenzene to remove zeolite impurities. The final conversion (based on the recrystallized BPBB) was 43%.

EXAMPLES 9 AND 10

Zeolites ELZ-20 and M-8, which had been used in earlier experiments, were reactivated by heating in air at 500° C. for 7 hr, cooled to 100° C., and sealed. Each of them was used as the catalyst according to the general procedure of Examples 4-6, the mole ratio of diphenyl ether to 1,4-benzenedicarbonyl chloride being in each case 53.2. The following conversions to BPBB were obtained;

| | |
|---|---|
| ELZ-20 | 65% |
| M-8 | 54%. |

EXAMPLE 11

"Zeolon" 900H zeolite from PQ Corporation was tested in a repetitive reaction and catalyst regeneration experiment. The same zeolite was used in all the runs, but it was regenerated prior to each reuse by heating in air at 500° C. for seven hours and was then cooled to room temperature. It was combined with diphenyl ether and 1,4-benzenedicarbonyl chloride so as to maintain in each run a ratio corresponding to 1 g of zeolite/1.5 g (0.0074 mole) of 1,4-benzenedicarbonyl chloride/77 g (0.452 mole) of diphenyl ether; the mixture was heated under nitrogen to 250° C. and held at that temperature for two hours. The zeolite was filtered off from the hot solution; the solution was cooled to 30° C., and the product BPBB was recovered by filtration. Since zeolite samples were removed for analysis before and after most of the runs, the amounts of the materials needed adjustment to maintain the desired weight ratios. The amounts of zeolite and conversion to BPBB in each run are given below.

| Run number | Zeolite, g | % Conversion |
|---|---|---|
| 1 | 30 | 57 |
| 2 | 26 | 49 |
| 3 | 24 | 37 |
| 4 | 21 | 41 |
| 5 | 17 | 40 |
| 6 | 17 | 47 |
| 7 | 15 | 50 |
| 8 | 13 | 38 |

This example shows that a mordenite zeolite can be regenerated and reused several times without significant loss of its catalytic activity.

EXAMPLE 12

Ten grams of a commerical 12-member ring zeolite LZ-Y52 (from Union Carbide) was suspended in 200 ml of water. The aqueous phase was acidified with sulfuric acid to a pH of less than 5 and then deaerated by bubbling nitrogen through it. The flask was stoppered and transferred to an inert atmosphere box, where 9 g of ferrous sulfate was added. The mixture was stirred overnight in the inert atmosphere box. It was then filtered and washed with 200 ml of deaerated water. This sequence of operations was performed four additional times. The iron-exchanged zeolite was removed from the inert atmosphere box and washed overnight with 200 ml of water in the presence of air. It was then filtered and dried at 108° C.

The above iron-exchanged zeolite was repeatedly used as a catalyst, without regeneration, in BPBB synthesis. In each one of twelve runs, a mixture of 319 g (1.873 mole) of diphenyl ether, 7.155 g (0.0352 mole) of 1,4-bezenedicarbonyl chloride, and 4.77 g of the catalyst (in the first run, then progressively decreasing to 3.70 g in the last run due to handling losses) was heated to 250° C. in a glass reactor, with a nitrogen purge. Two hours later, the zeolite was filtered off from the hot solution and either was stored for 1 to 16 hours in a vacuum oven at 130° C. or was immediately returned to the reactor for the next run.

The filtrate was allowed to cool. Crystals of BPBB began forming at about 115° C. and were recovered by filtration at 40° C., washed with methanol, and dried. High purity BPBB was recovered in each run, as shown below:

| Run number | % Conversion |
|---|---|
| 1 | 61.2 |
| 2 | 68.6 |
| 3 | 75.5 |
| 4 | 75.5 |
| 5 | 74.5 |
| 6 | 57.0 |
| 7 | 72.9 |
| 8 | 81.8 |
| 9 | 76.3 |
| 10 | 75.0 |
| 11 | 76.3 |
| 12 | 75.6 |

This example shows that an iron-exchanged zeolite can be used many times without regeneration without loss of catalytic activity or selectivity.

EXAMPLE 13

After the twelfth run of Example 12, the zeolite was dried in a vacuum oven at 130° C. for 16 hours; the dry weight was 3.70 g. This zeolite was used as the catalyst in the following reaction:

A mixture of 319 g (1.873 mole) of diphenyl ether, 21.465 g (0.1057 mole) of 1,4-benzenedicarbonyl chloride, and 3.70 g of the recovered zeolite was heated to 250° C. in a reactor with a nitrogen purge. After 270 minutes, the zeolite was filtered off from the hot solution, and the filtrate was allowed to cool. Crystals of BPBB began precipitating at about 140° C. The product was collected by filtration at 40° C., washed with methanol, and dried. It weighed 39.29 g, for a conversion of 79.0%.

EXAMPLE 14

Zeolite 13X (a 12-member ring zeolite from Union Carbide) was exchanged with iron using the procedure of Example 12. BPBB was made with this catalyst according to the process of Example 1, except that the reaction was run for 2 hours, instead of 6 hours. The dry product was impure, as determined by DSC, and weighed 2.98 g, for a conversion of 42.9%.

EXAMPLE 15

A 3 g portion of the iron-exchanged zeolite prepared for Example 14 was heated at 110° C. under a nitrogen purge and held at 110° C. for one hour; then, the temperature was increased to 250° C. Hydrogen chloride was passed through the zeolite for 4 hours at 250° C. The zeolite was allowed to cool to room temperature under a nitrogen purge.

BPBB was made with this zeolite using the procedure of Example 14. The dry product weighed 4.47 g, for a conversion of 64.3%, and had a high purity, as shown by DSC. This example shows that exposure of an iron-exchanged zeolite to hydrogen chloride improves its activity and selectivity.

EXAMPLE 16

Ten grams of Zeolon 900H mordenite was exchanged with iron according to the procedure of Example 12, except that the iron-exchanged zeolite was calcined after drying by heating in air at the rate of 60° C./hr to 550° C. and was held at 550° C. for 6 hours.

A mixture of 134 g (0.787 mole) of diphenyl ether, 3 g of 1,4-benzenedicarboyl chloride, and 2 g of the above zeolite was heated for 2 hours to 250° C. in a reactor under a nitrogen purge. The product was recovered as described in Example 12. It was pure BPBB, weighing 4.15 g, for a conversion of 59.7%.

EXAMPLE 17

Zeolite ELZ-20 (a zeolite Y from Union Carbide) was exchanged with iron as described in Example 16.

The procedure of Example 16 was repeated using the same amounts of the starting materials and of the zeolite. The dry BPBB, recovered from this reaction was pure and weighed 4.17 g, for a conversion of 60.0%.

We claim:

1. A catalytic process for the manufacture of 1,4-bis(4-phenoxybenzoyl)benzene, said process comprising contacting diphenyl ether for a period of about 40–360 min at a temperature of about 190°–250° C. with 1,4-benzenedicarbonyl chloride in the presence of a zeolite selected from the group consisting of:
   (a) activated zeolites in hydrogen-exchanged form having a ring structure containing 12 oxygen atoms and belonging to one of the classes of naturally occurring faujasites, naturally occurring mordenites, synthetic zeolites Y, and synthetic mordenites, and
   (b) iron-exchanged zeolites having a ring structure containing 12 oxygen atoms and belonging to one of the classes of naturally occurring faujasites, naturally occurring mordenites, synthetic zeolites X and Y, and synthetic mordenites,
   the weight ratio of 1,4-benzenedicarbonyl chloride to hydrogen-exchanged zeolite being about 3:1 to 1:2, and to iron-exchanged zeolite about 10:1 to 1:2, and the mole ratio of diphenyl ether to 1,4-benzenedicarbonyl chloride being about 15–80:1, when a hydrogen-exchanged zeolite is the catalyst and about 10–50:1 when an iron-exchanged zeolite is the catalyst,
   separating the zeolite from the resulting hot solution, cooling the hot solution to a temperature at which BPBB crystallizes, and separating the crystalline product from the cooled solution.

2. A process of claim 1, paragraph (a), wherein the mole ratio of diphenyl ether to 1,4-benzenedicarbonyl chloride is about 40–50:1.

3. A process of claim 1, paragraph (b), wherein the mole ratio of diphenyl ether to 1,4-benzenedicarbonyl chloride is about 15–20:1.

4. A process of claim 1 wherein the reaction temperature is held with the range of about 220°–250° C.

5. A process of claim 4 wherein the reaction time is about 60–150 minutes.

6. A process of claim 5, wherein the reaction temperature is about 250° C., and the reaction time is about 120 min.

7. A process of claim 1 wherein the solution remaining after the removal of the zeolite catalyst is cooled to about 25°–40° C. prior to the recovery of the crystalline product.

8. A process of claim 1 which is conducted at atmospheric pressure.

9. A process of claim 1 which is conducted at a reduced pressure.

10. A process of claim 9 which is conducted at a pressure at which diphenyl ether is refluxing.

11. A process of claim 1 which is a batch process.

12. A process of claim 11, in which an iron-exchanged zeolite catalyst is used repeatedly in successive batches.

13. A process of claim 1 which is a continuous process.

14. A process of claim 1 wherein the zeolite catalyst is a reused, hydrogen-exchanged regenerated catalyst which has been earlier used according to the process of claim 1.

15. A process of claim 1 wherein the catalyst is an iron-exchanged zeolite, which is calcined prior to use and heated in air for several hours.

16. A process of claim 1 wherein the catalyst is an iron-exchanged zeolite, which is heated for several hours prior to use in the presence of hydrogen chloride.

* * * * *